United States Patent [19]

Tenu et al.

[11] Patent Number: 4,663,311

[45] Date of Patent: May 5, 1987

[54] DERIVATIVES OF MURAMYL-PEPTIDES AND OF STEROIDS HAVING MACROPHAGE-ACTIVATING PROPERTIES

[76] Inventors: Jean P. Tenu, 3 Square des Colonnes, 92360 Meudon la Foret; Nigel C. Phillips, 29 Square des Maronniers, 78870 Bailly; Jean-François Petit, 24 rue Ernest Renan, 75015 Paris; Jean M. Bernard, 7 Square Couperin 18$^{e'}$et Residence du Parc Srcyz, 78330 Fontenay le Fleury, all of France

[21] Appl. No.: 641,457

[22] Filed: Aug. 16, 1984

[30] Foreign Application Priority Data

Aug. 16, 1983 [FR] France ................... 83 13333

[51] Int. Cl.$^4$ .................... A61K 31/56; C07J 9/00
[52] U.S. Cl. .......................... 514/26; 536/5
[58] Field of Search ............... 260/112.5 R; 514/26; 536/5

[56] References Cited

PUBLICATIONS

Parant et al., *Infection and Immunity*, 27(3), 826–831 (1980).
Masek et al., *Experientia*, 34(10), 1363–1364 (1978).
Lefrancier et al., *Biol. Abstr.*, 69(6), 4239 (1980), Abst. No. 39606.

*Primary Examiner*—Delbert R. Phillips
*Attorney, Agent, or Firm*—Weiser & Stapler

[57] ABSTRACT

The invention relates to compounds resulting from a covalent conjugation of the muramyl-peptide and the steroid particularly with membranal tropism, such as cholesterol, a precursor of its biosynthesis, or a steroid which is derived therefrom including a hydroxyl or amine group. Suspensions of liposomes including these compounds have macrophage activating properties.

13 Claims, No Drawings

DERIVATIVES OF MURAMYL-PEPTIDES AND OF STEROIDS HAVING MACROPHAGE-ACTIVATING PROPERTIES

The invention relates to derivatives of muramyl-peptides and of steroids, more particularly of sterols having macrophage-activating properties. It relates more particularly to compositions containing derivatives of muramyl-peptides and of steroids, preferably sterols, exerting a stimulation of the in vivo non-specific antitumoral resistance mechanisms.

The activation of macrophages is one of the principal mechanisms of antitumoral activity of immunomodulators: the activated macrophages are capable of destroying syngenic tumoral cells not only in vitro, but also in vivo (1). Reference will be made to the bibliography added at the end of this description as regards documents of the state of the art to which reference is made by means of numbers laced between parentheses.

It has been shown (2,3) that the muramylpeptides could increase the antitumoral activity of macrophages in vitro. It is not so in vivo when these substances are used in saline solution (4): this inactivity is doubtless due to the fact that the muramylpeptides penetrate slowly into the macrophages, probably through fluid pinocytosis (5), and that the muramylpeptides are rapidly eliminated from the organism through the kidney (6,7). It would then result from the conjunction of these two phenomena that the muramylpeptides injected in saline solution do not reach a sufficient concentration in the macrophages to be able to activate them.

Several solutions can be envisaged to overcome these drawbacks, in particular the encapsulation of muramylpeptides in liposomes which will be phagocyted and will deliver their contents inside the cell itself.

FIDLER and his collaborators developed this approach by the use of multi-lamellar liposomes composed of phosphatidylcholine (PC) and phosphatidylserine (PS) in a ratio 7/3 and including MDP; they thus succeeded in targeting this immunomodulator towards the circulating monocytes which are differentiated, under the influence of the MDP that they have endocyted, into activated macrophages (8,9,10).

The composition of liposomes and their nature (multilamellar) enable them to be directed, in particular, towards the capillaries of the pulmonary circulation (8,9,10). The monocytes which they have phagocyted then migrate into the lung where they are differentiated into activated macrophages: these activated macrophages are capable of destroying metastases of tumors with a pulmonary tropism like melanoma $B_{16}$ in the mouse (1, 4, 10).

However the use of soluble muramylpeptides runs up against numerous disadvantages: particularly those of the liposomes whose composition facilitates the targeting to the monocytes of the pulmonary circulation leak, that is to say they lose the encapsulated solution: this leakage is particularly marked with the liposomes PC/PS are contacted with serum.

These leakages on the other hand prevent good storage of the liposomes.

This drawback is partly overcome by the use of multilamellar liposomes. It may be thought that the most inner interlamellar spaces can contain or limit leakages before phagocytosis of the liposome. This modification results however in a loss of specificity of targeting. In fact the use of unilamellar liposomes or of liposomes comprising few lamallae could present advantages for targeting towards other organs than lung (8).

To overcome these drawbacks FIDLER and his collaborators have also already recommended the use of lipophile derivatives of N-acetyl-muramyl-L-alanyl-D-isoglutamine (MDP) or of N-acetyl-muramyl-L-alanyl-D-isoglutamyl-L-alanine (MTP), such as MTP-phosphatidyl-ethanolamine.

It is an object of the invention to overcome even more effectively the difficulties which have been mentioned above, in particular of providing novel derivatives of MDP possessing a considerable capacity of macrophage-activation, and more particularly of their in vivo tumoricidal activity, and this more particularly when they are administered in liposome form.

The derivatives of MDP according to the invention result essentially from a covalent conjugation of the MDP, of analogs or homologs of the latter, more generally of a muramyl-peptide and of a steroid with membranal tropism, such as cholesterol, a precursor of its biosynthesis, or again a steroid which is derived therefrom, or a similar molecule, these various possible residues having to include a hydroxyl or amine function.

Preferred compounds of the invention are characterized by the following general formula

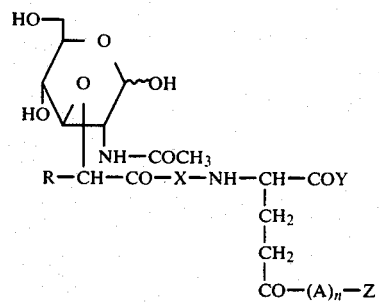

in which the substituents R, X, Y, A and Z have one of the following meanings:

R is either a hydrogen atom, or an alkyl group comprising from 1 to 5 carbon atoms;

X is an aminoacyl residue of the group comprising: L-alanyl, glycyl, L-valyl, L-isoleucyl, L-norleucyl, L-leucyl, L-seryl, L-threonyl, L-prolyl, L-glutaminyl, L-asparaginyl, L-methionyl, L-tryptophanyl, L-phenylalanyl, L-tyrosyl;

Y is an $NH_2$ or OH group, or again an alkyl residue comprising from 1 to 10 carbon atoms;

n=0 or a whole number from 1 to 5;

A is (when n takes the values of 1 to 5) an aminoacyl residue of the above-indicated group, but also of formula such as $-NH-(CH_2)_x-CO-$, with values of x comprised between 2 and 10, it being understood that the A groups present in the same compound can be identical or different;

Z is a derivative of 3-hydroxy-androstane or of 3-hydroxy-androstene bearing at $C_{17}$ a ketone function or a hydrocarbon chain comprising from 1 to 10, particularly from 2 to 8 carbon atoms.

Advantageously, said hydrocarbon chain is an aliphatic chain, as the case may be modified or substituted by one or several ketone-, ol-, amino groups.

The covalent bond between the muramyl-peptide and the derivative of 3-hydroxy-androstane or of 3-hydroxy-androstene is made preferably at the level of this hydroxy group.

It is preferable to use cholesterol, but also other sterols or steroids can be used to form the compounds according to the invention.

By way of example, there will be mentioned the sitosterols, stigmasterol, prgnenolone. It will be advantageous, each time that it is desired to target a particular organ, to employ in the constitution of the sterol muramylpeptide conjugate, those of the steroid hormones which are recognized, particularly by cellular specific recognition receptors of these organs. There will be mentioned for example androsterone and oestrone.

Particularly preferred compounds of the invention are constituted by the muramyl-dipeptide-($\gamma$)-L-alanyl-cholesterol-derived-esters and more particularly N-acetyl-muramyl-L-alanyl-D-isoglutaminyl-L-alanine-cholesterol ester, of the formula

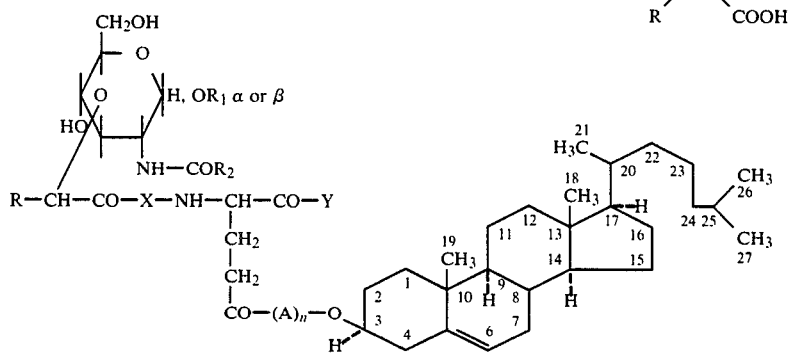

Preferably the compounds according to the invention are used in liposomes or suspensions of these liposomes in physiologically acceptable aqueous solutions, preferably sterile and isotonic, when these compositions are intended to be administered parenterally.

As regards the lipid compositions employed to form the liposomes, reference can be made to the literature, particularly that identified by the bibliographical references presented at the end of this description. Preferred lipid compositions are those which bring into play phospholipids, more particularly mixtures of phosphatidylcholine (PC) and phosphatidylserine (PS). Advantageously the liposomes are formed from mixtures containing the last mentioned phospholipids in a ratio of 7 volumes of PC to 3 volumes of PS or other proportions of lipids such as are used to make liposomes according to the target contemplated. The biological activities of the liposomes containing the derivatives of the invention are manifested both when the liposomes are presented in unilamellar or plurilamellar form.

Various routes are possible for obtaining a same compound. In all cases, the synthesis includes a series of steps in the course of which the various "fragments" constituting the overall structure of the compounds according to the invention are progressively assembled. The principal differences between the possible routes are found in the sequence selected for assembling the fragments. The reaction methods leading to the fixation of a fragment to the one or more contiguous fragments are on the whole little modified by the order in which this fixation is conducted, except of course that this order depends, on the one hand, on the choice of functional groups which react and which, consequently, must be free for the step concerned, and on the other hand, on the choice of the groups which must be blocked so as not to interfere in the course of this same step.

The preparation of the products according to the invention can be done from corresponding compounds of the muramylpeptide type. The production of the latter has been described in numerous publications, more particularly in that which relates to the preparations of muramic acid, of its analogs, or of its derivatives, which have in common the structure

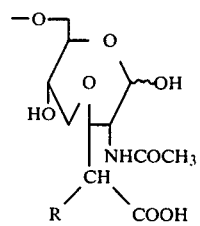

in which R has the previously indicated meaning.

Advantageously the compounds according to the invention can be synthesized by numerous methods. There are indicated below some preferred methods which can be used.

The fixation of a peptide chain to an N-acetyl-muramic acid derivative, or of an analog of the latter such as has been indicated above, is obtained by traditional methods in the field of peptide-synthesis. Such methods have been amply described in the prior literature and in particular in the French Patent applications whose references are recalled below.

Generally, the glycopeptide syntheses can be done either by fixing a first amino acid to the muramyl group, then by fixing to the compound so-obtained the second amino acid, and so on element by element. It is also possible to prepare separately the whole peptide chain amino acid by amino acid, then to fix the latter to the muramyl group. It is also possible to select intermediate processes in which fragments of the chain are prepared, then either to assemble these fragments to one another until the complete chain is formed which is then fixed to the muramyl group, or to fix a first fragment to the muramyl group, then a second to the product so-obtained etc. The choice of the sequence is guided principally by reasons of convenience or of yield.

The substitution Y is advantageously effected on the glutamyl group before synthesis of the chain. In the same way as n is equal or different from 0, the group Z is preferably first fixed to the terminal aminoacyl before the latter is integrated into the peptide chain.

The peptide syntheses are carried out according to traditional methods. By way of example, it is possible to select methods of activation of the carboxyls, like the method of activated esters or the mixed-anhydride methods or a method using a compound of the carbodiimide type such as N,N'-dicyclohexyl-carbodiimide or equivalent carbodiimides. A review of the traditional methods of peptide synthesis will be found in J. H. Jones, Chemistry and Industry, 723 (1974). Reference may also be made to the French patent applications already mentioned, or again to the following applications: 75 29624, 76 06819, 76 06820, 76 06821, 76 21889, 77 02646, and to the articles of LEFRANCIER et al. (Int. J. Peptide Protein Res., 1977, 9, 249 and 1978, 11, 289).

The formation of the esterified or amidated derivatives corresponding to the group Y is obtained in known manner. It is possible in particular to refer to the above-indicated French patent applications and particularly to applications 76 06820, 76 06821, 76 21889 and 77 02646.

To fix the residue Z through its hydroxyl funtion to the amino acid located at the C-terminal end of the peptide chain, one effects activation of the carboxyl group of this amino acid, by methods well known in peptide synthesis to lead to the formation of an ester linkage (see below).

(a) Synthesis-sequence-of the glycopeptide compounds corresponding to the alternative of the general formula in which n is different from zero The C-terminal amino acid is substituted at its amine function by a temporary protective group, such as t-butyloxycarbonyl (BOC), or any other group commonly utilised for this purpose in peptide synthesis. Its carboxyl group is then activated so as to be conjugated with the hydroxyl groups of the Z residue, thus forming an ester group. Various methods can be used: those with benzene sulfonyl chloride (M. Shemyakin, Angew. Chem. 72 (1960) 342), with mixed anhydrides (M. Brenner, J. P. Zimermann, P. Quitt, W. Schneider, and A. Hartmann, Helv. Chim. Acta. 40 (1951) 604), with carbonyldiimidazole (H. A. Staab, Rohr W, Mannschreck A. Angew, Chem. 73 (1961) 143), with activated esters in the presence of catalysts, such as hydroxybenzotriazole or imidazole (F. H. C. Stewart, Aust. J. Chem. 21 (1968) 1639); M. Chorev, Y. Knobler, Y. S. Klausner, J. chem. Research. (1977) 2246), that with dicyclohexylcarbodiimide in the presence of catalysts, such as dimethylaminopyridine (C. Gilon, A. Hassner, Y. Clausner, Tetrahedron Lett. 40 (1979) 3811).

The temporary protective group is then removed, by adequate methodology, for example, for the BOC—by the action of a normal solution of hydrochloric acid in glacial acetic acid. The derivative so obtained can be coupled according to methods known in peptide synthesis with a second acylaminoacid to give a dipeptide compound of the formula $A_2—A_1—Z—$. Thus there can be effected the synthesis of the peptide sequence of the claimed glycopeptide derivatives, by the sequential addition of each of the residues, then the synthesis of the glycopeptide derivatives themselves, by using, for example, α-O-benzyl-4.6-O-benzylidene-N-acetyl-muramic acid. The glycopeptide derivatives are finally obtained in a free state, after removal (by hydrogenolysis for example) of the protective groups.

Another preferred route, consists of coupling the α-substituted derivatives directly (through an amide or an ester, according to the general formula) of N-acetyl-muramyl-L-alanyl-D-glutamic acid with the residue H—(A)$_n$—Z, previously prepared, for example, but without being limiting, by using the mixed anhydride method.

(b) Sequence of synthesis of glycopeptide compounds corresponding to the alternative of the general formula in which n is equal to zero When n is equal to zero, the γ-carboxyl group of the D-glutamyl residue is engaged in an ester linkage with the residue Z. The methods described above (paragraph a) are then employed to prepare a derivative of the acyl-D-glutamic α-(amide or ester) γ-Z type, or indeed directly a dipeptide derivative of the acyl-X-D-glutamic α-(amide or ester) γ-Z type. These derivatives after removal of the acyl group, are coupled with suitable derivatives of muramic acid, such as α-O-benzyl-4-6-O-benzylidene-N-acetyl-muramic acid. The glycopeptide derivatives according to the invention are finally obtained after, for example, hydrogenolysis of the temporary protective groups.

Other characteristics of the invention will appear also in the cource of the description which follows, of one of its preferred examples, in the absence of any limiting intention.

(A) Preparation of N-acetyl-muramyl-L-alanyl-D-isoglutaminyl-L-alanyl-cholesterol ester (III)

(a) N-benzyloxycarbonyl-L-alanyl-cholesterol ester (I)

1.546 g (4 mmoles) of cholesterol, 1.12 g (5 mmoles) of Z-L-alanine, 500 mg (4 mmoles) of dimethylaminopyridine, are dissolved in 20 ml of dimethylformamide and 5 ml of tetrahydrofuran. At 0° C., 1.112 g (5.4 mmoles) of dicyclohexylcarbodiimide are added. The reaction mixture is stirred overnight, at ordinary temperature, then the precipitated dicyclohexylurea is filtered, and the filtrate concentrated to dryness. The residue obtained is taken up again in methylene chloride, then washed with NaHCO$_3$M, H$_2$O, KHSO$_4$ 5%, H$_2$O, and dried over MgSO$_4$. After concentration to dryness, the product is purified on a silica column, the elution being effected with the solvent system-toluene/ether (10/1, v/v). The fractions are tested by thin layer chromatography on silica gel in the solvent system benzene/ether (7/3 v/v), those containing the product being collected, concentrated and freeze-dried from their solution in dioxane: 1.63 g (70%)

$[\alpha]_D^{30°} = -32°$ (c=1, chloroform)

Elementary analysis: calculated for C$_{38}$H$_{57}$NO$_4$, 0.25 dioxane: C% 76.3—H% 9.7—N% 2.3; Found C% 76.3—H% 9.5—N% 2.3.

(b) L-alanyl-cholesteryl ester, acetate (II)

284 mg (0.48 mmoles) of N-benzyloxycarbonyl-L-alanyl-cholesterylester dissolved in 20 ml of dried and deperoxidized tetrahydrofuran and 3 ml of glacial acetic acid. Hydrogenation is continued for 2 hours in the presence of 300 mg of 5% Pd on carbon. The catalyst is filtered and the product after concentration is freeze-dried from its solution in dioxane: 226 mg (91%).

$[\alpha]_D^{25} = -18.75°$ (c=0.4, chloroform)

Elementary analysis: calculated for C$_{30}$H$_{51}$NO$_2$,CH$_3$COOH, 0.25 H$_2$O: C% 73.6—H% 10.7—N% 2.7; Found C% 73.5—H% 10.7—N% 2.5.

(c) N-acetyl-muramyl-L-alanyl-D-isoglutaminyl-L-alanyl-cholsteryl ester (III) (or MTP-Chol)

(1) 98.5 mg (0.2 mmoles) of N-acetyl-muramyl-L-alanyl-D-isoglutamine are incubated at ambiante temperature, for one hour, in 5 ml of dimethyl formamide, with 85 mg (0.2 mmoles) of N-cyclohexyl-N'-[β-(N-methylmorpholino)-ethyl]-carbodiimide, p-toluene sulfonate and 32 mg (0.2 mmoles) of hydroxybenzotriazole. Then 103.56 mg (0.2 mmoles) of L-alanyl-cholesteryl ester, acetate and 22 μl (0.2 mmoles) of N-methyl-morpholine, in 3 ml of methylene chloride are added. After 48 hours, the reaction mixture is concentrated to dryness and the product purified on a silicia column, the elution being effected with the solvent mixture chloroform/methanol (4/1 v/v): 45 mg (25%).

(2) 221.6 mg (0.45 mmoles) of N-acetyl-muramyl-L-alanyl-D-isoglutamine are taken up again and then concentrated to dryness, twice, with 20 ml of dry dimethylformamide. 2.5 ml of this solvent are finally added: to the solution cooled to $-15°$ C., are added 50 μl (0.45 mmoles) of N-methylmorpholine and 60 μl (0.45 mmoles) of isobutyl chloroformate. After 3 minutes, there is added in solution in 3 ml of tetrhydrofuran 210 mg (0.4 mmoles) of L-alanylcholesteryl ester, acetate and 45 μl (0.4 mmoles) of N-methylmorpholine. The mixture is left overnight at $-15°$, then concentrated to dryness and purified as described above. The product is obtained after freeze-drying from its solution in glacial acetic acid: 215 mg (57.7%).

The purity of the product is checked by thin layer chromatography on silica in the solvent system chloroform/methanol (4/1, v/v) and chloroform/tetrahydrofuran/methanol (5/2/1, v/v); and by determination of the amino acids and of the cholesterol.

$[\alpha]_D^{25} = +3.9$ (c=0.5 glacial acetic acid).

Elementary analysis: calculated for $C_{49}H_{81}N_5O_{12}, 2CH_3COOH, 1H_2O$: C% 59.5—H% 8.6—N% 6.6; Found C% 59.7—H% 8.5—N% 6.9.

(B) Biological properties of "MTP-chol"

(1) Preparation of the liposomes

The PC (distearoyl PC of CALIBIO-CHEM) and the PS (PS from ox brain of SIGMA) are dissolved in chloroform and supplemented with MTP-chol dissolved in ether/ethanol (4/1) in the proportion of 5 μg of MTP-chol per mg of PC+PS. The lipid solution so-obtained is placed in a flask and the solvents evaporated on a rotary evaporator so as to obtain a film on the surface of the flask.

The film is hydrated and shaken in a device of the VORTEX type in the presence of an isotonic solution of NaCl buffered with phosphate (PBS "Phosphate Buffered saline"); to which antibiotics are added. The liposomes so-obtained are centrifuged 30 minutes at 16,300 g then replaced in suspension in PBS+antibiotics so as to obtain a lipid concentration of 5 mg/ml.

Empty liposomes, that is to say without MTP-chol, are prepared under the same conditions and used as controls.

(2) Activation of macrophages by MTP-chol in liposomes

I. The microphages used are peritoneal macrophages from eight week old female BDF 1 mice. They have been brought into the peritoneal cavity by i.p. injection 4 days earlier, of 1.5 ml of a sterile inflammatory irritant, thioglycollate medium (marketed by Institut Pasteur Production).

The peritoneal cells are obtained by peritoneal washing with 5 ml of MEM medium (see below) of mice previously killed by cervical dislocation and bled by decapitation.

After centrifugation, they are replaced in suspension in MEM (Minimal Essential Medium, Institut Pasteur Production) supplemented with 5% of inactivated fetal calf serum (gibco), and antibiotics (penicillin+streptomycine).

The macrophages are identified by microscope by their aptitude to endocyte neutral red and counted on an aliquot portion.

The suspension is then adjusted to $2.10^6$ macrophages/ml and distributed in the proportion of 250 μl per cup in a Microtest II (NUNCLON) plastic box of 96 cups.

The disk is placed in an oven (HERAEUS) at 37° C. in an air atmosphere+5% water-saturated $CO_2$.

After incubation for 4 hours, the macrophages have adhered; the non-adherent cells (essentially lymphocytes) are removed by aspiration of the incubation medium (with a syringe) and two washings with PBS. The cups are then supplemented with 250 μl of medium containing liposomes or not (empty liposomes or liposomes containing MTP-chol).

After 24 hours of incubation the cups are washed with PBS then filled with 250 μl of a suspension of cells of mastocytoma $P_{815}$ ($0.3 \times 10^6$ cells/ml), supplemented with tritiated thymidine (Saclay) at a concentration of 1.2 μM (specific activity 1 Ci/mmole).

The $P_{815}$ mastocytoma is kept in ascites fluid by reinjection, every 11 days, in the peritoneal cavity of $DBA_2$ mice.

After 24 hours of coculture, the cells of each cup are collected on a glass fiber filter by means of a "collector" (SKATRON, LIERBYEN, Norway): in the course of this collection, made by washing of the cups, with a stream of distilled water, the DNA of the cells is released by lysis of the cells and fixed on the filter. If the cells of $P_{815}$ have multiplied, they are incorporated in tritiated thymidine and their DNA is radioactive, the radioactivity being proportional to the growth of the tumor (macrophages do not multiply under these conditions) (12).

The portion of filter corresponding to each cup is cut out and counted in the presence of scintillation liquid (LIPOLUMAC, LUMA) in a scintillation counter (RACKBETA, LKB). Each test is carried out in triplicate, the result concerned being the average of three cups.

The antitumoral activity of the macrophages is expressed as a percentage of growth inhibition: (%IC)

$$(\% IC) = \frac{T - X}{T} \times 100$$

T=incorporation of thymidine in the untreated macrophage coculture+tumoral cells
X=incorporation of thymidine in the treated macrophage coculture+tumoral cells.

The table below gives the % of growth inhibition of Mastocytoma $P_{815}$ cocultured in the presence of macrophages treated by empty liposomes or liposomes containing 5 μg of MTP-chol/mg of lipids.

TABLE

|  |  | 400 μg lipids/ml % PC | 200 μg lipids/ml % PC |
|---|---|---|---|
| Empty liposomes | 1st test | 0 | 10.7 |

TABLE-continued

|  |  | 400 µg lipids/ml % PC | 200 µg lipids/ml % PC |
|---|---|---|---|
|  | 2nd test | 1 | 11.5 |
| Liposomes + 5 µg MTP-chol/mg of lipid | 1st test | 60 | 64.6 |
|  | 2nd test | 63 | 71.5 |
| MDP in solution 50 µg/ml |  |  | 18 |

The presence of MTP-chol in the liposomes, at a concentration of 2 µg/ml (400 µg liposomes/ml of medium) or 1 µg/ml (200 µg liposomes/ml of medium) activates the macrophages significantly more than 50 µg of MDP does.

II. Activation of macrophages by MTP-chol in cytotoxic activity-liposomes

The macrophages used are alveolar macrophages of F344 male rats of 200 gm. The macrophages are obtained by washing the lung with 9×5 ml of PBS medium of DULBECCO without calcium or magnesium, of rats anesthesitized with 0.5 ml 5% Nembutal ip (Laboratoires Abbott S.A.) and bled by incision of an artery of the kidney. After centrifugation, they are resuspended in MEM (Minimal Essential Medium) supplemented with 5% of inactivated fetal calf serum (Gibco), glutamine, sodium pyruvate, non-essential amino acids, vitamins and antibiotics (penicillin and streptomycine).

The suspension is then adjusted to 5×10⁵ macrophages/ml and redistributed in the proportion of 100 µl per cup in a TITERTEK plastic dish of 96 cups. After incubation for 4 hours, the macrophages have adhered; the non-adherent cells (less than 5%) are removed by aspiration of the medium and two washings with incubation medium. The cups are then supplemented with 200 µl of the medium containing or not liposomes (empty or containing MTP-chol) or not or MDP in solution.

After 24 hours of incubation of the macrophages, the cups are washed 3 times, then filled by 100 µl medium. The cups are then supplemented with 100 µl of a suspension of cells of the B16-BL6 melanoma ($5 \times 10^4$ cells/ml) labelled with $^{125}$I-deoxyuridine.

The B16-BL6 melanoma, a sub-line of B16 melanoma, is maintained in culture in vitro.

After 96 hours of coculture, the dead cells are removed by 3 washings of each cup with 200 µl of PBS of DULBECCO medium. The cups are then supplemented with 200 µl of 0.5M NaOH. The DNA of the cells is freed by lysis of the cells. If the cells are killed by the macrophages, their DNA is released into the medium, and removed by the washings before the addition of NaOH (Effects of liposome structure and liposome composition on the activation of the tumoricidal properties of macrophages by liposomes containing muramyl dipeptide. Schroit, A. J. and Fidler, I. J. Cancer Research, 42, 161–167 (1982)). The radioactivity remaining in each cup is counted in a gamma counter (BECKMAN GAMMA 4000). Each test is done in triplicate, the result corresponds to the average of three cups.

The antitumoral activity of the macrophages in expressed as a cytotoxicity percentage (%CYT):

$$\% CYT = \frac{T - X}{T} \times 100$$

where
T = $^{125}$I-deoxyuridine remaining in the untreated macrophages + tumoral cells coculture; and
X = $^{125}$I-deoxyuridine remaining in the treated macrophages + tumoral cells coculture.

TABLE

The table gives the %CYT of the B16-BL6 melanoma cocultivated in the presence of macrophages treated by liposomes or liposomes containing 0.04, 0.4 and 4.0 µg MTP-mg phospholipid.

The presence of MTP-chol in the liposomes, at a concentration of more than 0.017 µg/ml (400 µg phospholipid/ml) or than 0.0017 µg/ml (40 µg phospholipid/ml) significantly activates the macrophages. The same degree of activation is obtained for the MDP in solution at a concentration of 10 to 500 µg/ml.

| Treatment |  | % CYT, 400 µg | | % CYT, 40 µg | |
|---|---|---|---|---|---|
|  |  | MTP-chol µg/ml | phospholipid/ml | MTP-chol µg/ml | phospholipid/ml |
| empty liposome | 1st test | — | 6 | — | 0 |
|  | 2nd test | — | 9 | — | 0 |
| Liposomes + 4 µg MTP-chol/mg of phospholipid | 1st test | 1.7 | 30 | 0.17 | 54 |
|  | 2nd test |  | 38 |  | 52 |
| Liposomes + 0.4 µg MTP-chol/mg of phospholipid | 1st test | 0.17 | 23 | 0.017 | 21 |
|  | 2nd test |  | 29 |  | 18 |
| Liposomes + 0.04 µg MTP-chol/mg of phospholipid | 1st test | 0.017 | 9 | 0.0017 | 17 |
|  | 2nd test |  | 16 |  | 14 |

| Concentration of MDP in solution | Degree of macrophag-activation |
|---|---|
| 500 µg/ml | 52 |
| 100 µg/ml | 32 |
| 10 µg/ml | 18 |
| 1 µg/ml | 6 |
| 0.1 µg/ml | 0 |

The results obtained with one of the representatives of the class of compounds according to the invention show that the conjugation of a sterol with a muramyl peptide render the latter particularly suitable for activating macrophages to confer on them a strong antitumoral activity, after easy inclusion of this conjugate in liposomes.

It is to be noted also that the sterol-muramylpeptide conjugates have also preserved the adjuvant properties and, at the same time, anti-infectious properties (particularly with respect to Klebsiella) characteristic of MDP.

III—The antiviral properties of the compounds of the invention

The compounds according to the invention have also anti-viral properties, as demonstrated by the results of the tests which follow, with respect to one of the representative compounds of the class according to the invention, namely MTP-cholesterol.

The anti-viral activity has been evaluated in an experimental infection system. Swiss mice aged 10 weeks were used. The virus chosen was that of the influenza virus A/PR 8.

At day D-0, the animals received by the intra-nasal route 50 microliters of a viral dilution at $1/10^4$.

An anti-viral activity of the tested compound has been found both in preventive and curative experiments (prevention). The administration of one mg of compound by the intra-nasal route one day prior to the viral dilution produced the survival of 67% of the animals.

When the compounds were used at the curative level, the best results were obtained when 0.5 mg of the compound was administered sub-cutaneously one day after the administration of the viral dilution. 71% of the animals survived.

These results thus underlined the interest of the localized administration routes of the compound, particularly for obtaining a prophylactic effect, in addition to the showing of the curative anti-viral activity of MTP cholesterol. The local route is likely to enable a more direct stimulation of the immunitary defense mechanisms at the level of the mucous membranes. This is of particular significance, taking into account the interest of this administration route in the treatment of viral pathology.

The invention also relates to biological reagents which can be constituted by means of the compounds according to the invention. These reagents are useful as reference or comparison compounds for the study of the macrophage-activating properties of compounds under study.

The invention also relates to pharmaceutical compositions which contain at least one of the compounds or a pharmaceutically acceptable salt thereof associated with pharmaceutically acceptable carriers or diluents, particularly for stimulating the immunitary defenses, particularly the anti-infectious antiviral and antitumoral resistances of the host to whom (or which) they are administered.

The pharmaceutical compositions of the invention can be administered to a host—animal or human being—in any suitable manner for obtaining the desired effect.

The invention relates more particularly to pharmaceutical compositions, based on liposomes, formed with physiologically acceptable lipids, into which the compounds of the invention are incorporated, if need be, in association with other active substances.

Advantageous pharmaceutical compositions are constituted by injectable suspensions of liposomes containing an effective dose of at least one compound according to the invention. Preferably, these suspensions are produced in an isotonic sterile aqueous phase, preferably saline or glucosed solution.

The invention relates more particularly to such suspensions which are suitable for administration by intradermal, intramuscular, sub-cutaneous or intravenous injection or also by scarification.

The invention also relates to pharmaceutical compositions, preferably in the form of liposomes, administrable by other routes, particularly by the oral or rectal route, or again in forms suitable for contact with the mucous membranes, particularly the ocular, nasal, pulmonary or vaginal mucous membranes.

Consequently, it relates to pharmaceutical compositions in which one at least of the compounds according to the invention is associated with pharmaceutically acceptable excipients, solids or liquids, suitable for the constitution of oral, ocular or nasal administrative forms or with excipients adapted for the constitution of rectally administrable forms, or again with excipients, for example gelatinous ones, suitable for vaginal administration. They relate finally to compositions intended for the pulmonary route, particularly solutions prepared for administration by means of a conventional aerosol device.

By way of examples of doses which can be administered, to reinforce to antiviral and antitumoral defenses of the host, will be mentioned doses of 0.1 to 1,000 μg per kg body weight, for example 0.1 to 100 μg when the administration is made parenterally, or again a dose of 1 to 1,000 μg per kg body weight, by the oral route. These doses are expressed in terms of the MDP included in the liposome.

These compositions can be used for intralesional injections into tumors of the mammary type, melanomas and other solid tumors.

The invention is obviously not limited to the embodiments described above by way of examples and the man skilled in the art will be able to contrive alternatives thereof without however departing from the scope of the claims.

In particular, the claims encompass all sterol-muramyl-peptide-conjugates whose formulae distinguish only from those directly included in the claims by substitutions which have only secondary importance. By way of examples of of such equivalent compounds one may mention those in which the saccharide nucleus of the muramyl-peptide is substituted, for example on the 6 position. Different substituants (whether on the 6-position or another position of the saccharide nucleus, or also on the peptidic chain) have been exemplified in the above French patents or foreign counterpart patents, all of which are incorporated herein by reference. Other equivalent sterol-muramylpeptide conjugates encompassed by the claims are those in which the linkage between the peptide group and the sterol group is formed via an ol function—or a different function—located in a position other than the 3 position on the polynuclear nucleus, or again on the carbon chain possibly fixed to the nucleus at the 17 position.

Finally it will obviously be understood that the claims also encompass all salts that the compounds can form, particularly the pharmaceutically acceptable salts thereof.

There follows the bibliography to which reference was made in the present application. The articles concerned are also incorporated by reference herein.

BIBLIOGRAPHY

1. I. J. Fidler, Z. Barnes, W. E. Fogler, R. Kirsh, P. Bugelski and G. Poste

Involvement of macrophages in the eradication of established metastases following intravenous injection of liposomes containing macrophage activator Cancer Res., 42, 496–501 (1982).

2. D. Juy and L. Chedid

Comparison between macrophage activation and enhancement of non-specific resistance to tumors by mycobacterial immunoadjuvants.

Proc. Nat. Acad. Sci., 72, 4105–4109 (1975).

3. J. P. Tenu, E. Lederer and J. F. Petit

Stimulation of thymocyte mitogenic protein secretion and of cytostatic activity of mouse peritoneal macrophages by trehalose dimycolate and muramyldipeptide.

Eur. J. Immunol., 10, 647–653 (1980).

4. I. J. Fidler, S. Sone, W. E. Fogler and Z. L. Barnes

Eradication of spontaneous metastases and activation of alveolar macrophages by intravenous injections of liposomes containing muramyl dipeptide.

Proc. Natl. Acad. Sci. USA, 78, 1680–1684 (1981).

5. J. P. Tenu, A. C. Roche, A. Yapo, C. Keida, M. Monsigny and J. F. Petit

Absence of cell surface receptors for muramylpeptides in mouse peritoneal macrophages.

Biol. Cell, 44, 157–164 (1982).

6. M. Parant, F. Parant, L. Chedid, A. Yapo, J. F. Petit and E. Lederer

Fate of the synthetic immunoadjuvant, muramyl dipeptide ($^{14}$C-labelled) in the mouse.

Int. J. Immunopharmac., 1, 35–41 (1979).

7. A. Yapo, J. F. Petit, E. Lederer, M. Parant, F. Parant and L. Chedid

Fate of two $^{14}$C labelled muramyl peptides: Ac-mur-L-Ala-γ-D-Glu-meso-A$_2$PM and Ac-Mur-L-Ala-γ-D-Glu-meso-A$_2$PM-D-Ala-D-Ala in mice.

Evaluation of their ability to increase non specific resistance to *Klebsiella* infection.

Int. J. Immunopharmac., 4, 143–149 (1982).

8. G. Poste, C. Bucana, A. Raz, P. Bugelski, R. Kirsh and I. J. Filder

Analysis of the fate of systematically administered liposomes and implicatio for their use in drug delivery.

Cancer Res., 42, 1412–1422 (1982).

9. A. J. Schroit and I. J. Fidler

Effects of liposome structure and lipid composition on the activation of the tumoricidal properties of macrophages by liposomes containing muramyl dipeptide.

Cancer Res., 42, 161–167 (1982).

10. A. J. Schroit, E. Galligioni and I. J. Fidler

Factors influencing the in situ activation of macrophages by liposomes containing muramyl dipeptide.

Biol. Cell, 47, 87–94 (1983).

11. A. J. Schroit and I. J. Fidler

Stimulation of macrophage-mediated destruction of tumor cells by liposomes containing a lipophilic derivative of muramyl dipeptide.

In E. Serou (ed.) Current concepts in human immunology and cancer immunomodulation, pp. 631–637, New York, Elsevier Biomedical Press, B. V., 1982.

12. M. Lepoivre, J. P. Tenu, G. Lamaire and J. F. Petit

Antitumor activity and hydrogen peroxide release by macrophages elicited by trehalose diesters.

J. of Immunol., 129, 860–866 (1982).

What is claimed is:

1. A muramyl peptide covalently linked to a steroid having the formula

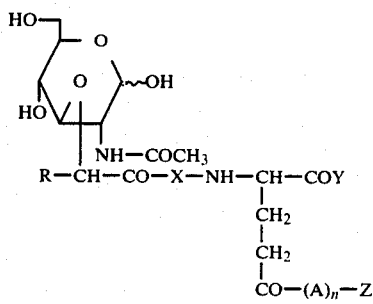

wherein

R is hydrogen, or an alkyl group having from 1 to 5 carbon atoms,

X is an aminoacyl residue selected from the group of L-alanyl, glycyl, L-valyl, L-isoleucyl, L-norleucyl, L-leucyl, L-seryl, L-threonyl, L-prolyl, L-glutamyl, L-asparaginyl, L-methionyl, L-tryptophanyl, L-phenyl-alanyl, and L-tyrosyl, Y is NH$_2$, OH, or an alkyl group from 1 to 10 carbon atoms, n is 0 or a whole number of 1 to 5, A is an aminoacyl residue of the above-indicated group, or a residue of formula —NH—(CH$_2$)$_x$—CO—, wherein x is from 2 to 10, and wherein when x is from 2 to 5, A is identical or different, Z is 3-hydroxy androstane or 3-hydroxy-androstene having at C$_{17}$ a substituent selected from the group consisting of a ketone or hydrocarbon chain having from 1 to 10 carbon atoms, wherein Z is covalently bonded to the muramyl peptide at the 3-hydroxy group.

2. The compound of claim 1 wherein the hydrocarbon chain has from 2 to 8 carbon atoms.

3. The compound of claim 1 which has the formula

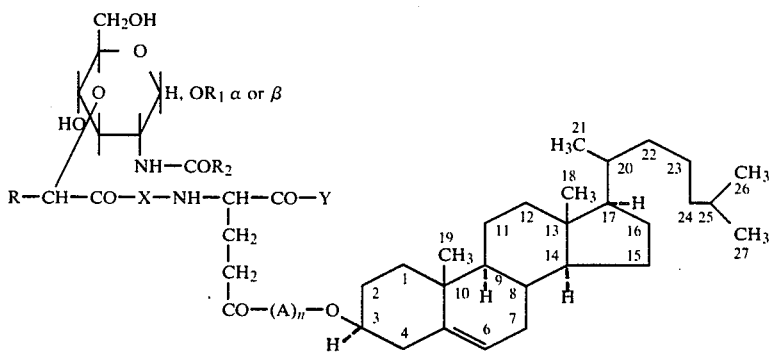

wherein:
R$_1$ is hydrogen;
R$_2$ is —CH$_3$,
n is 0 or a whole number of 1 1 to 5
A is an aminoacyl residue of the above-identified group, or a residue of the formula —NH—(CH$_2$)$_x$—CO—, wherein x is from 2 to 10 and wherein when x is from 2 to 5, A is identical or different.

4. The compound of claim 1 which is N-acetyl-muramyl-L-alanyl-D-isoglutaminyl-L-alanyl-3-cholesterol ester.

5. A liposome of the compound of claim 1.

6. The liposome of claim 5 which is unilamellar or plurilamellar.

7. The liposome of claim 5 which contain phosphatidylcholine (PC) and phosphatidylserine (PS) in the ratio of 7 volumes of PC to 3 volumes of PS.

8. A pharmaceutical composition which is effective to activate macrophages in vitro which comprises a pharmaceutically acceptable carrier and a therapeutically effective amount of the compound of claim 1.

9. A pharmaceutical composition which is effective to activate macrophages in vitro which comprises a pharmaceutically acceptable carrier and the liposome of claim 5.

10. The composition of claim 9 which is a suspension of the liposome.

11. The composition of claim 10 which is an aqueous suspension of the liposome.

12. The composition of claim 11 which is injectable.

13. The compound of claim 1 wherein the steroid is selected from the group consisting of cholesterol, sitosterol, stigmasterol, pregnanolone, androsterone and estrone.

* * * * *